(12) United States Patent
Lau et al.

(10) Patent No.: US 11,819,243 B2
(45) Date of Patent: Nov. 21, 2023

(54) MEDICAL SHEATH AND RELATED SYSTEMS AND METHODS

(71) Applicant: Boston Scientific Medical Device Limited, Ballybrit (IE)

(72) Inventors: Kaylie Lau, Toronto (CA); Eduardo Moriyama, Richmond (CA); Gareth Davies, Toronto (CA); Christian Balkovec, Kitchener (CA)

(73) Assignee: Boston Scientific Medical Device Limited, Galway (IE)

( * ) Notice: Subject to any disclaimer, the term of this patent is extended or adjusted under 35 U.S.C. 154(b) by 395 days.

(21) Appl. No.: 16/823,547

(22) Filed: Mar. 19, 2020

(65) Prior Publication Data
US 2021/0290268 A1 Sep. 23, 2021

(51) Int. Cl.
*A61B 17/34* (2006.01)
*A61B 17/00* (2006.01)

(52) U.S. Cl.
CPC .... *A61B 17/3478* (2013.01); *A61B 2017/003* (2013.01); *A61B 2017/00247* (2013.01); *A61B 2017/3488* (2013.01)

(58) Field of Classification Search
CPC ...... A61B 17/3478; A61B 2017/00247; A61B 2017/003; A61B 2017/3488
See application file for complete search history.

(56) References Cited

U.S. PATENT DOCUMENTS

| | | |
|---|---|---|
| 3,448,739 A | 6/1969 | Stark et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |

(Continued)

*Primary Examiner* — Ashley L Fishback
(74) *Attorney, Agent, or Firm* — Nelson Mullins Riley & Scarborough

(57) ABSTRACT

A medical sheath includes an elongate member having a proximal portion defining a proximal end and a distal portion defining a distal end. A first lumen extends through the elongate member and is open at the proximal and the distal end for passage of a medical device through the lumen. The medical sheath further includes an anchoring mechanism that is deployable from the elongate member. The anchoring mechanism includes an anchor that is removably securable to an anatomical feature to secure the elongate member to the anatomical feature, and a connector securing the anchor to the elongate member.

11 Claims, 9 Drawing Sheets

(56) References Cited

U.S. PATENT DOCUMENTS

| | | |
|---|---|---|
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Ivinston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |

(56) References Cited

U.S. PATENT DOCUMENTS

| | | |
|---|---|---|
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McLntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III. |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0228223 A1* | 9/2008 | Alkhatib ............... A61F 2/2457 606/221 |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0137394 A1* | 6/2011 | Lunsford ............ A61B 17/1114 606/45 |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |
| 2018/0028790 A1* | 2/2018 | Bar-Cohen ......... A61B 17/3421 |
| 2018/0242978 A1* | 8/2018 | Chou ............... A61B 17/12109 |
| 2019/0021763 A1 | 1/2019 | Zhou et al. |
| 2019/0247035 A1 | 8/2019 | Gittard et al. |

* cited by examiner

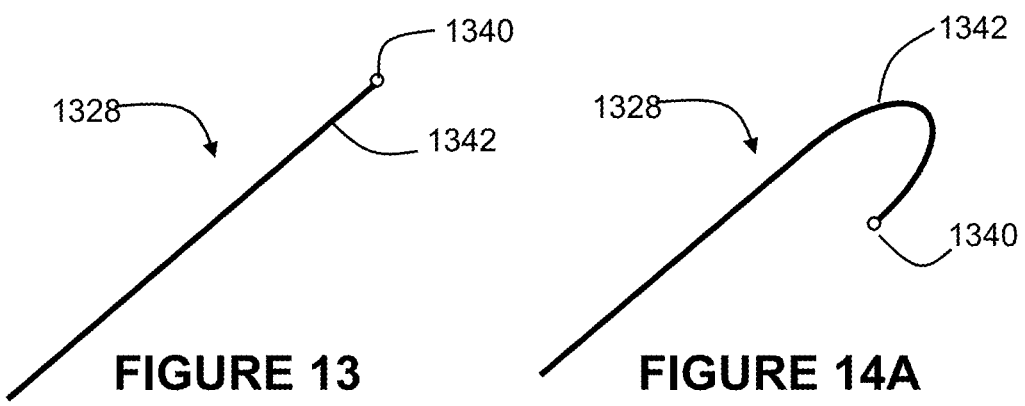
FIGURE 13
FIGURE 14A
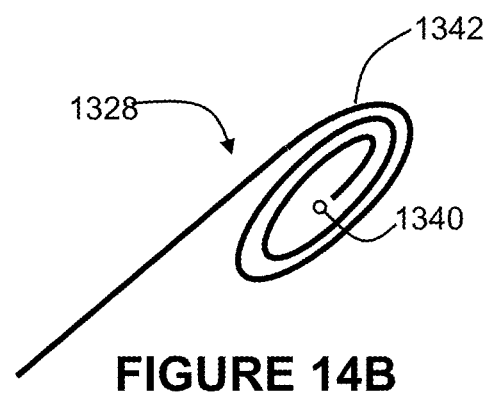
FIGURE 14B
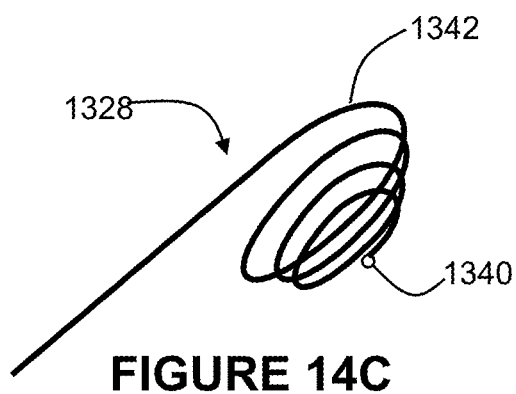
FIGURE 14C

MEDICAL SHEATH AND RELATED SYSTEMS AND METHODS

FIELD

This document relates to medical procedures such as transseptal perforation. More specifically, this document relates to sheaths for use in medical procedures, and related systems and methods.

SUMMARY

The following summary is intended to introduce the reader to various aspects of the detailed description, but not to define or delimit any invention.

Medical sheaths are disclosed. According to some aspects, a medical sheath includes an elongate member having a proximal portion defining a proximal end and a distal portion defining a distal end. A first lumen extends through the elongate member and is open at the proximal and the distal end for passage of a medical device through the lumen. An anchoring mechanism is deployable from the elongate member and includes an anchor that is removably securable to an anatomical feature to secure the elongate member to the anatomical feature, and a connector securing the anchor to the elongate member.

In some examples, the medical sheath further includes a second lumen that extends through the elongate member and is open at the distal portion. The anchor can be movable between a storage position in which the anchor is housed within the second lumen and a deployed position in which the anchor is outside of the second lumen. The sheath can further include a first actuator that is actuatable to move the anchor between the storage position and the deployed position. When in the deployed position, the anchor can be spaced radially from the elongate member.

In some examples, the anchor is movable between a lock configuration for securing to the anatomical feature and a release configuration for releasing the anatomical feature. The sheath can include a second actuator that is actuatable to move the anchor between the lock configuration and the release configuration. The anchor can include a clamp for clamping onto the anatomical feature. In the lock configuration, the clamp can be closed, and in the release configuration, the clamp can be open.

In some examples, the anchoring mechanism further includes a perforating tip for perforating the anatomical feature. The anchor can include an expandable structure, and the expandable structure can be expanded when the anchor is in the lock configuration and can be retracted when the anchor is in the release configuration In some examples, the sheath includes a handle secured to the proximal portion of the elongate member. The connector can include a wire secured at a first end to the handle and at a second end to the anchor.

Methods for carrying out medical procedures are also disclosed. According to some aspects, a method for carrying out a medical procedure includes a. intravenously advancing a sheath toward a target region in a patient's body; b. securing an anchor of the sheath to an anatomical feature proximate the target region; c. advancing a medical device through a first lumen of the sheath towards the target region; and d. with the anchor of the sheath secured to the anatomical feature, performing a medical procedure on the target region using the medical device.

In some examples, the target region is a fossa ovalis of the patient's heart and the anatomical feature is a limbus of the fossa ovalis.

In some examples, the medical device is a perforation device, and step d. includes perforating the fossa ovalis.

In some examples, between steps a. and b., the method further includes deploying the anchor from a second lumen of the sheath.

In some examples, step b. includes clamping the anchor onto the anatomical feature.

In some examples after step d., the method further includes releasing the anchor from the anatomical feature and retracting the anchor into the sheath.

In some examples, step b. includes creating a perforation in the anatomical feature, passing the anchor through the perforation, and expanding the anchor. Step b. can include using a radiofrequency perforation electrode to create a perforation in the anatomical feature. After step d., the method can include retracting the anchor and withdrawing the anchor from the perforation.

Transseptal perforation systems are also disclosed. According to some aspects, a transseptal perforation system includes a sheath. The sheath includes an elongate member having a proximal portion defining a proximal end and an opposed distal portion defining a distal end. A first lumen extends through the elongate member and is open at the proximal end and the distal end. An anchoring mechanism is deployable from the elongate member and includes an anchor that is removably securable to an anatomical feature to secure the elongate member to the anatomical feature, and a connector securing the anchor to the elongate member. The system further includes a dilator advanceable through the lumen from the proximal end to the distal end and having a dilating tip. The system further includes a perforation device advanceable through the dilator towards the dilating tip and having a perforating tip.

BRIEF DESCRIPTION OF THE DRAWINGS

The accompanying drawings are for illustrating examples of articles, methods, and apparatuses of the present disclosure and are not intended to be limiting. In the drawings:

FIG. 13 is a partial side view of another example anchoring mechanism, in a release configuration;

FIG. 14A is a partial side view of the anchoring mechanism of FIG. 13, in a lock configuration;

FIG. 14B is a partial side view of the anchoring mechanism of FIG. 13, in an alternative lock configuration;

FIG. 14C is a partial side view of the anchoring mechanism of FIG. 13, in a further alternative lock configuration;

DETAILED DESCRIPTION

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein are sheaths that can be used in medical procedures, such as cardiac procedures. For example, the sheaths can be used in transseptal perforation procedures, in which the sheath is advanced to the right atrium of a patient's heart via the femoral vein, and a perforation device (e.g. a radiofrequency (RF) perforation device or a mechanical perforation device) and dilator are guided through the sheath, to the right atrium. When the sheath is adjacent a target region in the right atrium, for example the fossa ovalis of the atrial septum, the perforation device can be advanced out of the sheath and used to create a perforation in the target region, and the dilator can be advanced out of the sheath to dilate the perforation. Such procedures can be carried out, for example, as a medical treatment, or to gain access to the left atrium for a subsequent medical treatment.

Figure 1:
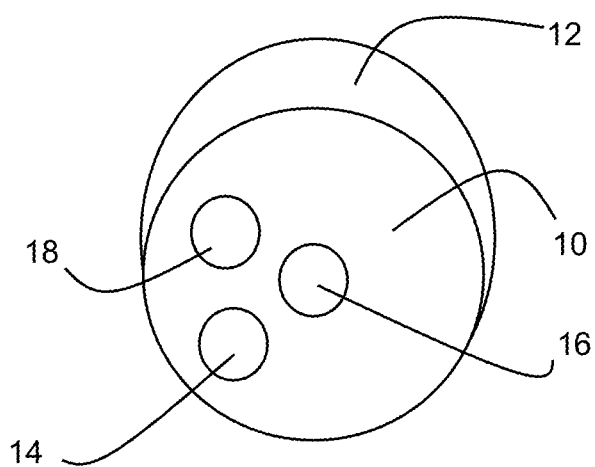
FIG. 1 is a schematic front view of a fossa ovalis and limbus of an atrial septum, showing example desired regions for perforation.

The sheaths disclosed herein are configured to anchor to (i.e. be physically secured to) an anatomical feature proximate the target region. For example, in transseptal perforation procedures in which the target region for perforation is the fossa ovalis, the sheath can anchor to the limbus of the fossa ovalis. Anchoring to an anatomical feature can physically stabilize the sheath, which can prevent unintended movement of the sheath, and can in turn facilitate precise positioning of the sheath. For example, in transseptal perforation procedures, depending on the purpose of the procedure, it can be desired to perforate the fossa ovalis at different locations. Referring to FIG. 1, which schematically shows a fossa ovalis 10 and limbus 12 in some instances, it can be desired to perforate the fossa ovalis 10 at a first location 14; in other instances, it can be desired to perforate the fossa ovalis 10 at a second location 16; and in yet other instances, it can be desired to perforate the fossa ovalis 10 at a third location 18. By anchoring the sheath to the limbus 12, the sheath is physically stabilized, which can facilitate precise positioning of the sheath at the first location 14, second location 16, or third location 18.

Figure 2:
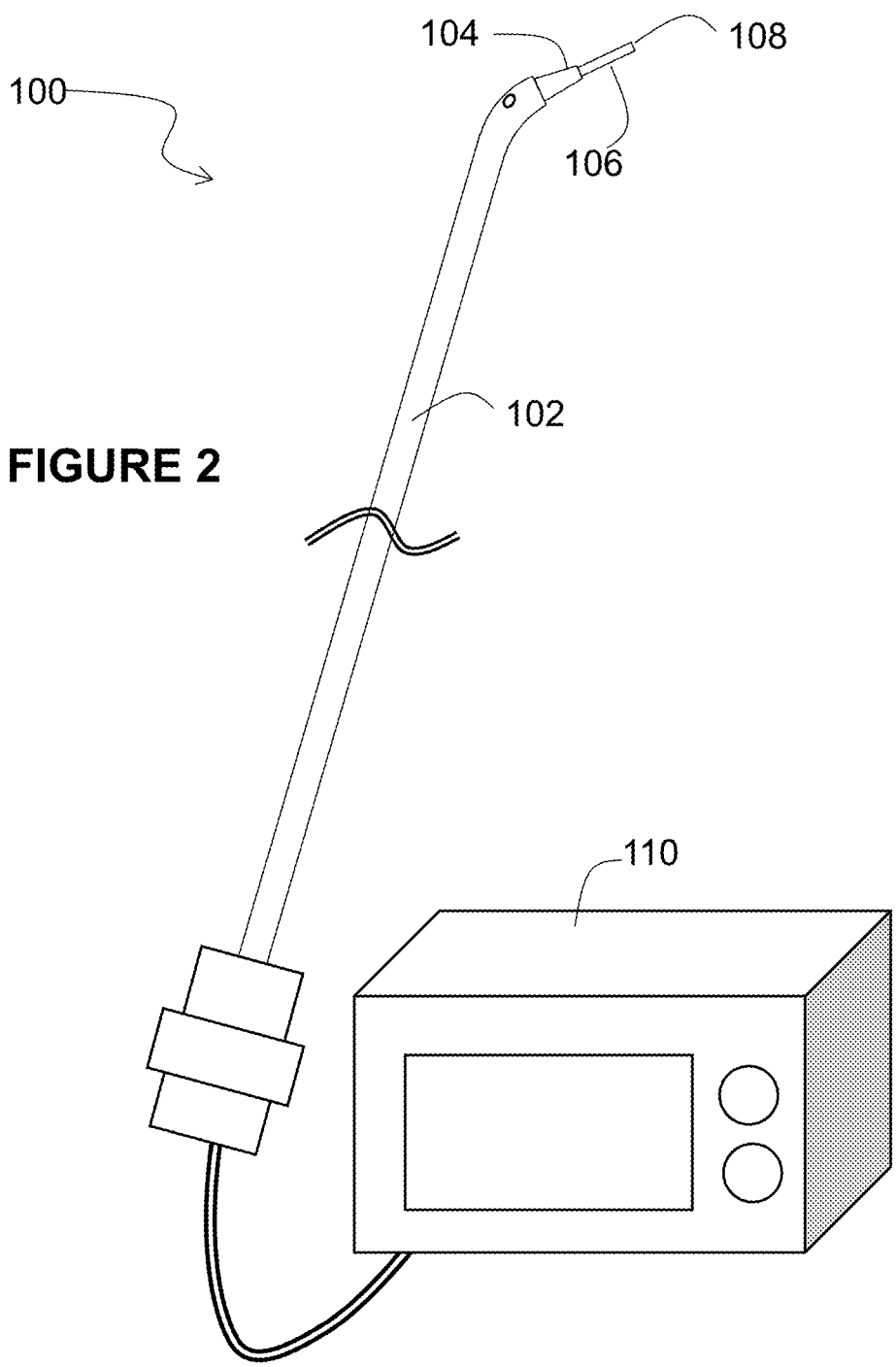
FIG. 2 is a perspective view of a system for transseptal perforation.

Referring now to FIG. 2, an example medical system 100 is shown. In the example shown, the system 100 is a transseptal perforation system, for advancing towards a patient's heart and perforating a fossa ovalis of the patient's heart. The system 100 includes a sheath 102 (also referred to herein as a 'medical sheath'), a dilator 104, and a perforation device 106 having a perforating tip 108. In the example shown, the perforation device 106 is a radiofrequency (RF) perforation device, and the perforating tip 108 includes a radiofrequency perforation electrode.

In use, the sheath 102 can be advanced intravenously via the femoral vein towards the right atrium of the patient's heart. The dilator 104 and perforation device 106 can both be advanced towards the patient's heart via the sheath 102. The RF perforation device 106 can be connected to a radiofrequency generator 110, which can in turn be connected to one or more grounding pads (not shown). When in the desired position in the patient's heart, for example adjacent the fossa ovalis, the RF perforation device 106 can be activated to perforate the fossa ovalis.

Figure 3:
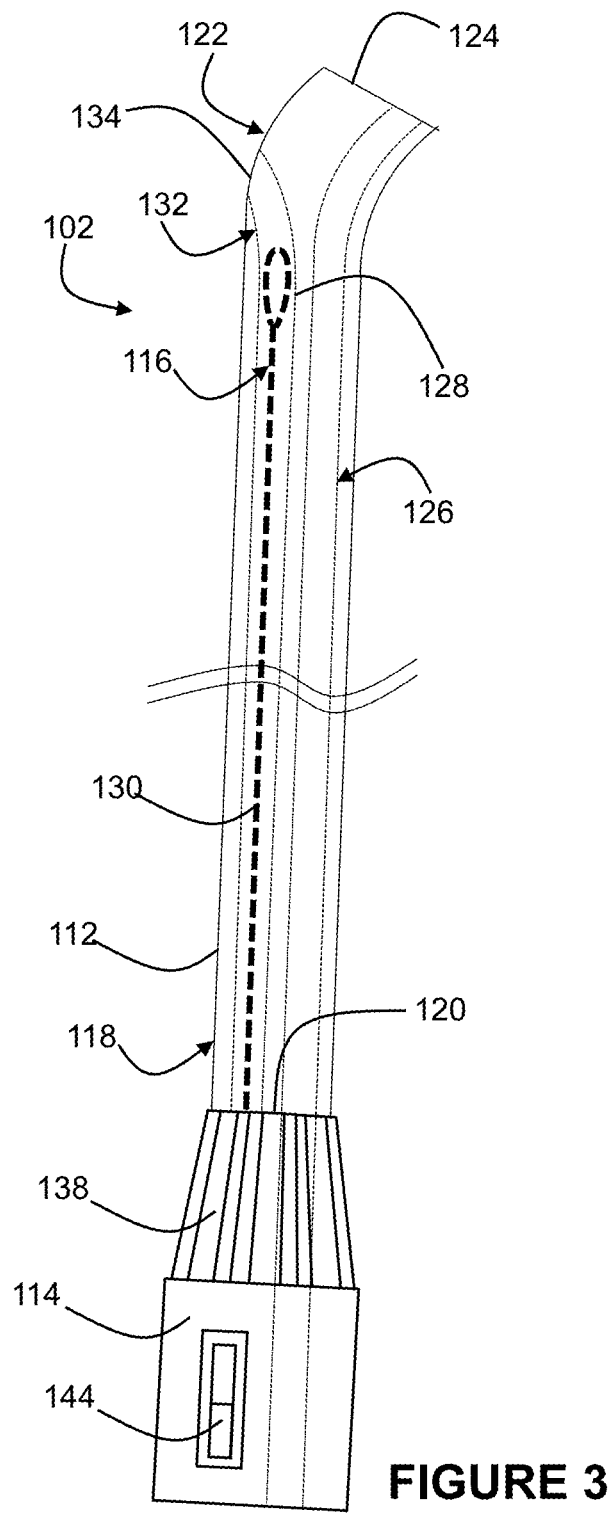
FIG. 3 is a front view of a sheath of the system of FIG. 2, showing a first lumen, second lumen, and anchoring mechanism in dotted line.
Figure 4:
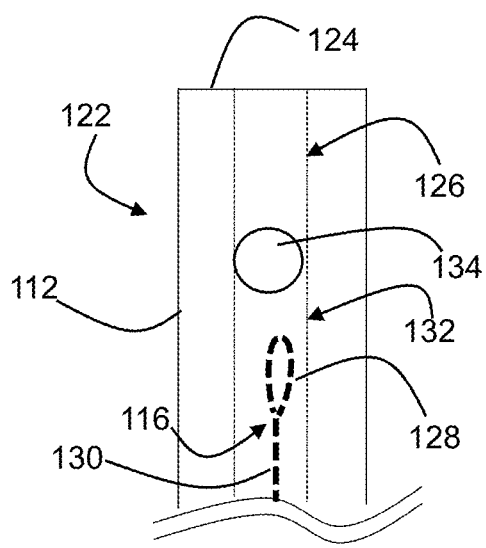
FIG. 4 is a partial side view of the sheath of FIG. 3, showing the first lumen, second lumen, and anchoring mechanism in dotted line.
Figure 5:
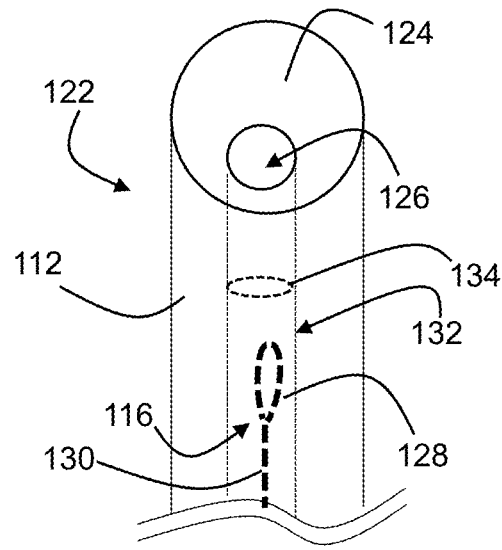
FIG. 5 is an end view of the sheath of FIG. 3, showing the first lumen, second lumen, and anchoring mechanism in dotted line.

Referring to FIGS. 3 to 5, the sheath 102 is shown in greater detail. In the example shown, the sheath 102 generally includes an elongate member 112, a handle 114, and an anchoring mechanism 116 (which is shrouded within the elongate member 112 and shown in dotted line in FIGS. 3 to 5). The elongate member 112 has a proximal portion 118 that defines a proximal end 120 of the elongate member 112, and a distal portion 122 that defines a distal end 124 of the elongate member 112. The handle 114 is secured to the proximal portion 118 of the elongate member 112. A first lumen 126 (shown in dotted line) extends through the elongate member 112 from the proximal end 120 to the distal end 124, for passage of a medical device (e.g. dilator 104 and/or perforation device 106) through the elongate member 112.

Referring still to FIGS. 3 to 5, as mentioned above, the anchoring mechanism 116 is securable to an anatomical feature, to anchor the sheath 102 to that anatomical feature and provide physical stability to the sheath 102. The anchoring mechanism 116 is deployable from the sheath 102 and generally includes an anchor 128, which can be any suitable structure that is removably securable to an anatomical feature, and a connector 130, which connects the anchor 128 to the elongate member 112. The connector 130 can connect the anchor 128 directly to the elongate member 112, or can connect the anchor 128 indirectly to the elongate member 112 (e.g. by connecting the anchor 128 to the handle 114, which is in turn connected to the elongate member 112).

Referring still to FIGS. 3 to 5, in the example shown, the elongate member 112 includes a second lumen 132 (shown in dotted line) that extends through the elongate member 112 from the distal portion 122 to the proximal end 120, for storage of the anchoring mechanism 116. The second lumen 132 is open at a side surface of the elongate member 112, at opening 134.

Figure 6:
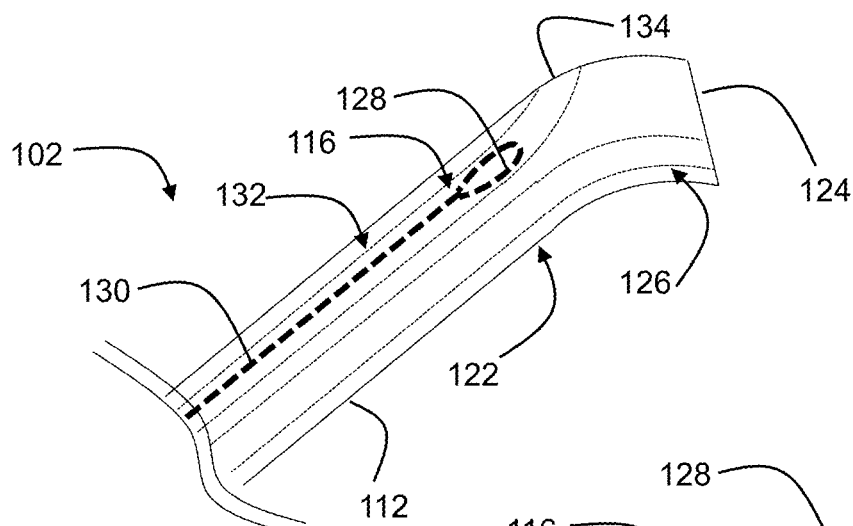
FIG. 6 is a partial side view of the sheath of FIG. 2, showing the first lumen, second lumen, and anchoring mechanism in dotted line, and showing the anchoring mechanism in a storage position.
Figure 7:
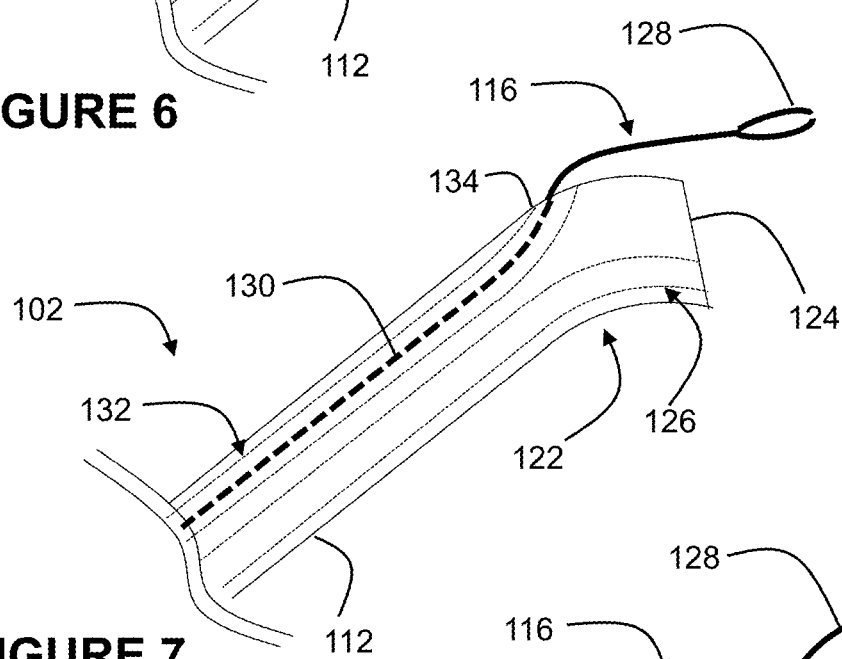
FIG. 7 is a partial side view of the sheath of FIG. 2, showing the first lumen, second lumen, and anchoring mechanism in dotted line, and showing the anchoring mechanism in a deployed position and in a lock configuration.

Referring to FIGS. 6 and 7, the anchor 128 is movable between a storage position, shown in FIG. 6, in which the anchor 128 is housed within the second lumen 132, and a deployed position, shown in FIG. 7, in which the connector 130 passes through the opening 134 to position the anchor 128 outside of the second lumen 132, to be secured to an anatomical feature.

Referring still to FIGS. 6 and 7, in the example shown, the connector 130 is in the form of a resiliently flexible wire. The wire has a first end (not shown) that is secured to the handle 114, and a second end that is secured to the anchor 128. The wire can be shaped so that when the anchor 128 is in the deployed position, the anchor 128 is spaced radially from the elongate member 112 (e.g. the wire can be made from a shape memory material). Alternatively, the wire can be steerable (e.g. using a steering mechanism that is controlled via a control in the handle 114).

Referring back to FIG. 3, the sheath 102 further includes an actuator for moving the anchor 128 between the storage and deployed positions. In the example shown, the actuator is part of the handle 114, and includes a rotatable dial 138. Rotating of the dial 138 in a first direction (e.g. clockwise) causes the connector 130 to be drawn inwardly into the second lumen 132 towards the handle 114, to move the anchor 128 to the storage position. Rotating of the dial 138 in a second direction (e.g. counter-clockwise) causes the connector 130 to be fed outwardly from the second lumen 132 through the opening 134, to move the anchor 128 to the deployed configuration.

Figure 8:
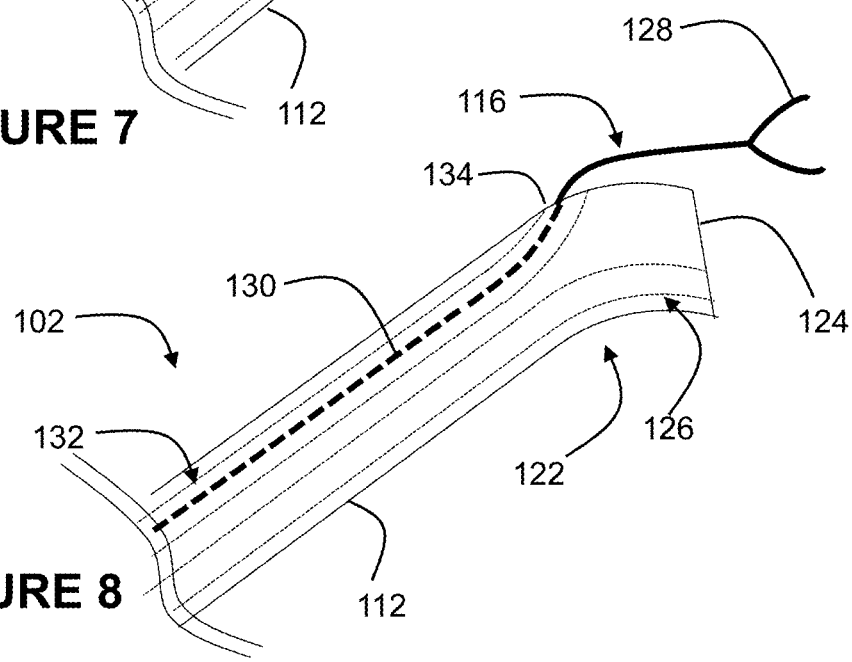
FIG. 8 is a partial side view of the sheath of FIG. 2, showing the first lumen, second lumen, and anchoring mechanism in dotted line, and showing the anchoring mechanism in the deployed position and in a release configuration.

Referring now to FIGS. 7 and 8, the anchor 128 is movable between a lock configuration, shown in FIG. 7, for securing to the anatomical feature, and a release configuration, shown in FIG. 8, for releasing the anatomical feature. In the example shown, the anchor is in the form of a clamp, for clamping onto the anatomical feature. In the lock configuration, the clamp is closed and held in the closed position, and the release configuration, the clamp is open.

Figures 9, 10:
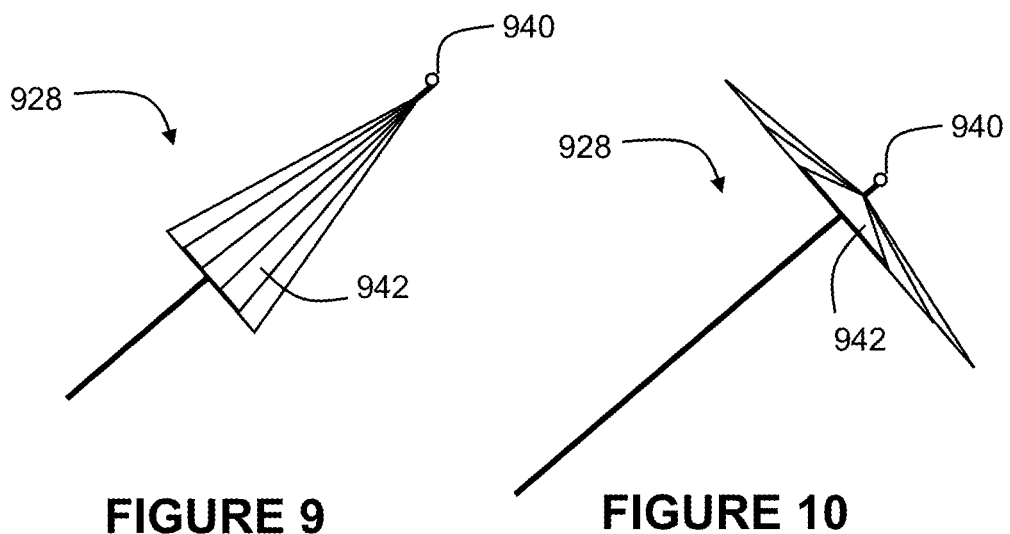
FIG. 9 is a partial side view of another example anchoring mechanism, in a release configuration.
FIG. 10 is a partial side view of the anchoring mechanism of FIG. 9, in a lock configuration.
Figures 11, 12:
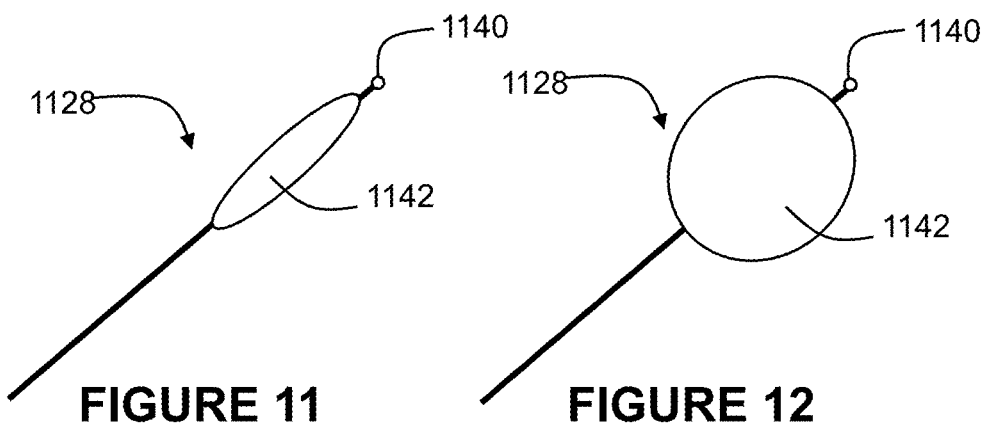
FIG. 11 is a partial side view of another example anchoring mechanism, in a release configuration.
FIG. 12 is a partial side view of the anchoring mechanism of FIG. 11, in a lock configuration.

Various alternative configurations of the anchor are possible. For example, the anchor can include a perforating tip (in such examples, the perforating tip of the perforation device can be referred to as a first perforating tip, and the perforating tip of the anchor can be referred to as a second perforation tip). for perforating the anatomical feature (e.g. the limbus of the fossa ovalis), and an expandable structure that can be passed through the perforation and expanded to prevent the anchor from being withdrawn back through the perforation. The perforating tip can include a mechanical perforating tip, or a radiofrequency perforation electrode. Examples of such anchors are shown in FIGS. 9 to 114C. In the example of FIGS. 9 and 10, the anchor 928 includes a radiofrequency perforation electrode 940, and an umbrella-like structure 942 that is expandable and retractable. The radio frequency electrode 940 can perforate the anatomical feature, and the structure 942 can pass through the perforation while in the retracted configuration (shown in FIG. 9). Once the structure 942 has passed through the perforation, it can be expanded to the expanded configuration (shown in FIG. 10), to secure the anchor 928 against the anatomical feature. In the example of FIGS. 11 and 12, the anchor 1128 includes a radiofrequency perforation electrode 1140, and a balloon-like structure 1142 that is inflatable and deflatable. The radiofrequency perforation electrode 1140 can perforate the anatomical feature, and the structure 1142 can pass through the perforation while in the deflated configuration. Once the structure 1142 has passed through the perforation, it can be inflated, to secure the anchor 1128 against the anatomical feature. In the example of FIGS. 13 and 14A to C, the anchor 1328 includes a radiofrequency perforation electrode 1340 and a steerable or shape memory wire 1342 that can be steered from a straight configuration (shown in FIG. 13) to a curved configuration (shown in FIG. 14A), or from a straight configuration to a spiral configuration (shown in FIG. 14B), or from a straight configuration to a pigtail configuration (shown in FIG. 14C). The radiofrequency perforation electrode 1340 can perforate the anatomical feature, and the wire 1342 can pass through the perforation while in the straight configuration. Once the wire 1342 has passed through the perforation, it can be steered to the curved or spiral or pigtail configuration, to secure the anchor 1328 against the anatomical feature. In further examples, the anchor can include more than one wire (e.g. two steerable or shape memory wires) In the examples of FIGS. 9 to 14C, the sheath 102 can be connected to the RF generator, to power the radiofrequency perforation electrode (940, 1140, 1340).

Referring back to FIG. 3, in the example shown, the sheath 102 further includes a second actuator 144 for moving the anchor 128 between the lock configuration and the release configuration. In the example shown, the second actuator 144 is on the handle 114, and includes a switch. Actuating the switch can cause the anchor 128 to move between the lock configuration and the release configuration (e.g. can cause the clamp to open and close). In alternative examples, a single actuator can move the anchor between the storage position and the deployed position and also between the lock configuration and the release configuration.

A method for carrying out a medical procedure, and specifically for transseptal perforation, will now be described with reference to FIGS. 15 to 19. The method will be described with reference to the system 100 of FIG. 2; however, the system 100 of FIG. 2 can be used according to different methods, and the method can employ different systems.

As a first step (not shown), a guidewire can be advanced via the femoral vein towards the heart, and "parked" in the superior vena cava (SVC). The dilator 104 can then be inserted into the sheath 102, with the tip of the dilator 104 shrouded within the sheath 102. With the anchor 128 in the storage position, the sheath 102 and dilator 104 can then be intravenously advanced towards the SVC, over the guidewire. The guidewire can then be removed.

As a second step (not shown), the perforation device 106 can be advanced through the first lumen 126 of the sheath, via the dilator 104, until the perforating tip 108 is just shy of the distal end of the dilator 104.

Figure 15:
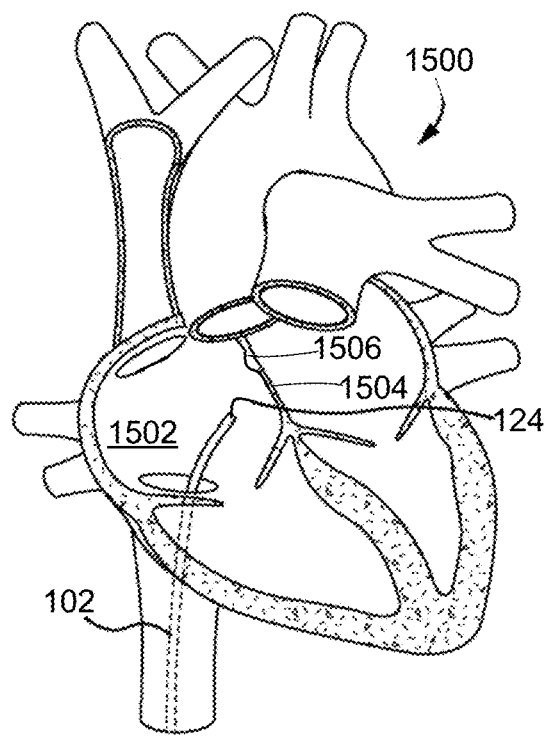
FIG. 15 is a schematic view of a step of a method for transseptal perforation, using the system of FIG. 2.

Referring to FIG. 15, as a third step, the distal end 124 of the sheath 102 can then be advanced towards a target region in the patient's heart 1500, e.g. to the right atrium 1502 of the patient's heart 1500, to position the distal end 124 of the sheath 102 adjacent the target region. In the example shown, the target region is the fossa ovalis 1504 of the atrial septum.

Figure 16:
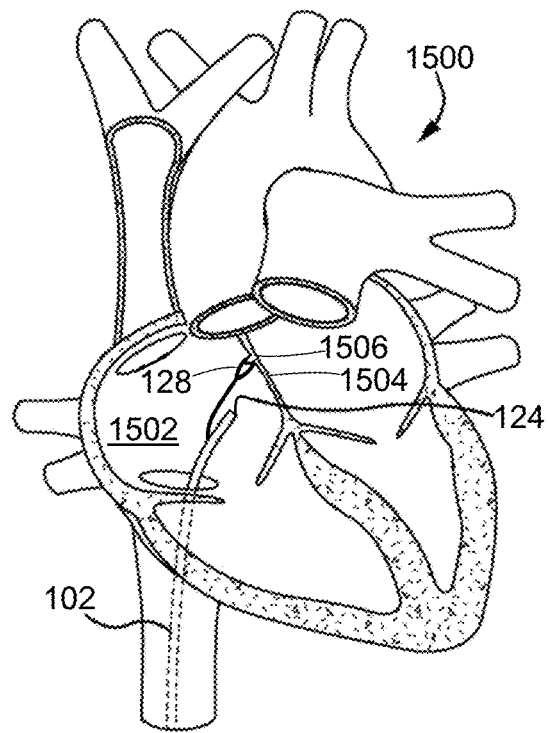
FIG. 16 is a schematic view of a subsequent step of the method of FIG. 15.
Figure 17:
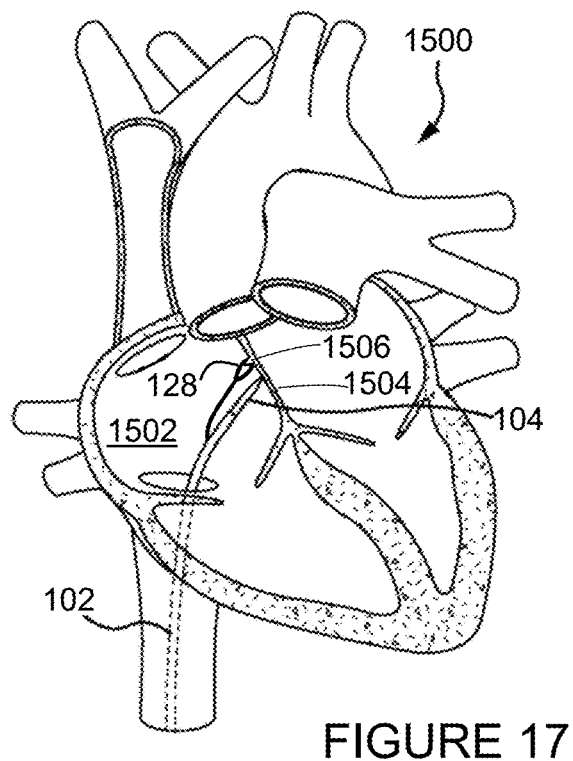
FIG. 17 is a schematic view of a subsequent step of the method of FIGS. 15 and 16.

Referring to FIG. 16, the anchor 128 can then be secured to an anatomical feature proximate the target region. In the present example, the anatomical feature is the limbus 1506 of the fossa ovalis 1504. This can be done by actuating the first actuator (i.e. the dial 138, not shown in FIG. 16) to deploy the anchor 128 from the second lumen 132 (not shown in FIG. 16), via the opening 134 (not shown in FIG. 16), and then actuating the second actuator 144 (not shown in FIG. 16) to clamp the anchor 128 onto the limbus 1506 of the fossa ovalis 1504. Optionally, this step can be carried out under fluoroscopy or using another imaging modality, to facilitate securing of the anchor 128 to the anatomical feature.

Figure 20:
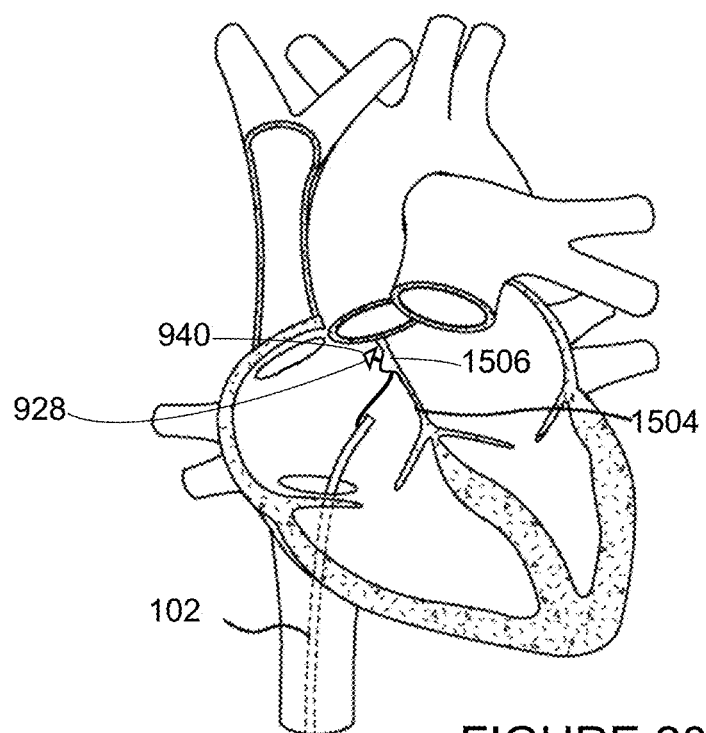
FIG. 20 is a schematic view of a step another method for transseptal perforation.

In alternative examples (e.g. examples using the devices of FIGS. 9 to 14), the limbus 1506 can be perforated using an RF electrode of the anchoring mechanism, and the anchor can then be passed through the perforation and expanded. Such an example is shown in FIG. 20, in which the anchor 928 of FIGS. 9 and 10 is shown deployed from the sheath 102 and in the expanded configuration, with the radiofrequency perforation electrode 940 passed through the limbus 1506 of the fossa ovalis 1504.

Figure 18:
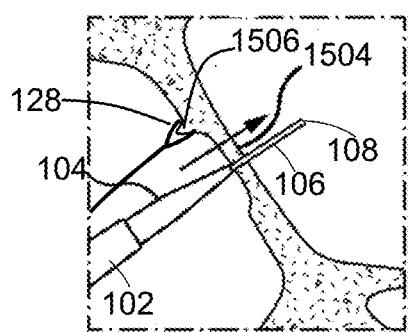
FIG. 18 is a schematic view of a subsequent step of the method of FIGS. 15 to 17.

Referring back to FIG. 16, with the anchor 128 secured to the anatomical feature, the sheath 102 can be precisely positioned at a desired location (e.g. adjacent one of the locations 14, 16, 18 described above with reference to FIG. 1). As mentioned above, by having the sheath 102 anchored to the anatomical feature, the sheath 102 is physically stabilized, which can allow for precise positioning of the sheath 102 at the desired location. When the sheath 102 is at the desired location, the fossa ovalis 1504 can be perforated. Particularly, referring to FIG. 17, the dilator 104 can be advanced so that the dilating end thereof is proud of the sheath 102, and the perforation device 106 (not visible in FIG. 17) can be advanced so that the perforating tip 108 is proud of or flush with the dilator 104 and is adjacent the fossa ovalis 1504. The RF generator 112 (not shown in FIGS. 15 to 19) can then be engaged, to supply power to the RF electrode of the perforating tip 108. Referring to FIG. 18, the perforating tip 108 can then be advanced through the fossa ovalis 1504.

Once the fossa ovalis 1504 has been perforated, the anchoring mechanism 128 can be released from the limbus 1506. In the example shown, the anchoring mechanism 128 can be released from the limbus 1506 by actuating the second actuator 144 (not shown in FIGS. 15 to 19) to move the clamp to the open configuration, and then actuating the first actuator (i.e. dial 138, not shown in FIGS. 15 to 19) to retract the clamp back into the second lumen 132. In examples involving an anchoring mechanism that includes a radiofrequency perforation electrode (i.e. the examples of FIGS. 9 to 14), the anchor can be retracted, and then withdrawn back through the perforation, into the second lumen.

Figure 19:
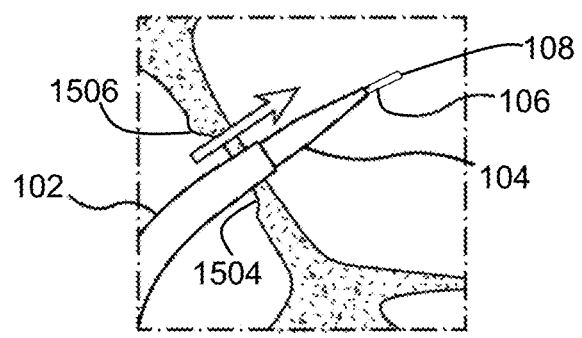
FIG. 19 is a schematic view of a subsequent step of the method of FIGS. 15 to 18.

Referring to FIG. 19, the dilator 104 can then be advanced from the sheath 102 to dilate the perforation, and the sheath 102 can then be advanced through the perforation, to the left atrium. Once access to the left atrium has been gained, a subsequent medical treatment (not shown) can be carried out.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A transseptal perforation system comprising:
   a perforation device; and
   a medical sheath comprising:
   an elongate member having a proximal portion defining a proximal end and a distal portion defining a distal end, and a first lumen extending through the elongate member and open at the proximal and the distal end for passage of the perforation device through the lumen; and
   an anchoring mechanism that is deployable from the elongate member and comprises an anchor that is removably securable to an anatomical feature to secure the elongate member to the anatomical feature for facilitating positioning of the sheath and providing stability to the perforation device for perforating a tissue, and a connector for securing the anchor to the elongate member;
   wherein the anchor is an expandable structure movable between a lock configuration for securing to the anatomical feature and a release configuration for releasing the anatomical feature;
   wherein the expandable structure is expanded when the anchor is in the lock configuration and is retracted when the anchor is in the release configuration; and wherein the anchoring mechanism further comprises a perforating tip for perforating the anatomical feature.

2. The system of claim 1, further comprising a second lumen extending through the elongate member and open at the distal portion, wherein the anchor is movable between a storage position in which the anchor is housed within the second lumen and a deployed position in which the anchor is outside of the second lumen.

3. The system of claim 2, further comprising a first actuator actuatable to move the anchor between the storage position and the deployed position.

4. The system of claim 2, wherein when in the deployed position, the anchor is spaced radially from the elongate member.

5. The system of claim 1, further comprising a handle secured to the proximal portion of the elongate member, wherein the connector comprises a wire secured at a first end to the handle and at a second end to the anchor.

6. A transseptal perforation system, comprising
   a sheath comprising i) an elongate member having a proximal portion defining a proximal end and an opposed distal portion defining a distal end, and a first lumen extending through the elongate member and open at the proximal end and the distal end, and ii) an anchoring mechanism that is deployable from the elongate member and comprises an anchor that is removably securable to an anatomical feature to secure the elongate member to the anatomical feature for facilitating positioning of the sheath, and a connector for securing the anchor to the elongate member, wherein the anchor is a clamp for clamping onto the anatomical feature, the clamp movable between a locked configuration wherein the clamp is closed for securing to the anatomical feature and a release configuration wherein the clamp is open for releasing the anatomical feature;

a dilator advanceable through the lumen from the proximal end to the distal end and having a dilating tip; and a perforation device advanceable through the dilator towards the dilating tip and having a perforating tip, wherein the anchor provides stability to the perforation device when the anchor is removably secured to an anatomical feature.

7. A transseptal perforation system comprising:

a perforation device; and a medical sheath comprising:

an elongate member having a proximal portion defining a proximal end and a distal portion defining a distal end, a first lumen extending through the elongate member and open at the proximal and the distal end for passage of the perforation device through the lumen, and a second lumen extending through the elongate member and open at the distal portion;

an anchor configured to be movable from a storage position in the second lumen and a deployed position outside the second lumen, the anchor further configured to be movable between a lock configuration for securing to an anatomical feature for facilitating positioning of the sheath and a release configuration;

a first actuator configured to move the anchor between the storage position and the deployed position; and a second actuator actuatable to move the anchor between the lock configuration and the release configuration.

8. The system of claim 7, wherein when in the deployed position, the anchor is spaced radially from the elongate member.

9. The system of claim 7, wherein the anchor comprises a clamp for clamping onto the anatomical feature, and wherein in the lock configuration the clamp is closed and in the release configuration the clamp is open.

10. The system of claim 7, wherein the anchor comprises a perforating tip for perforating the anatomical feature.

11. The system of claim 7 further comprising a handle secured to the proximal portion of the elongate member.

* * * * *